May 24, 1966 E. S. BOERNER Plant Pat. 2,634
ROSE PLANT
Filed April 23, 1965
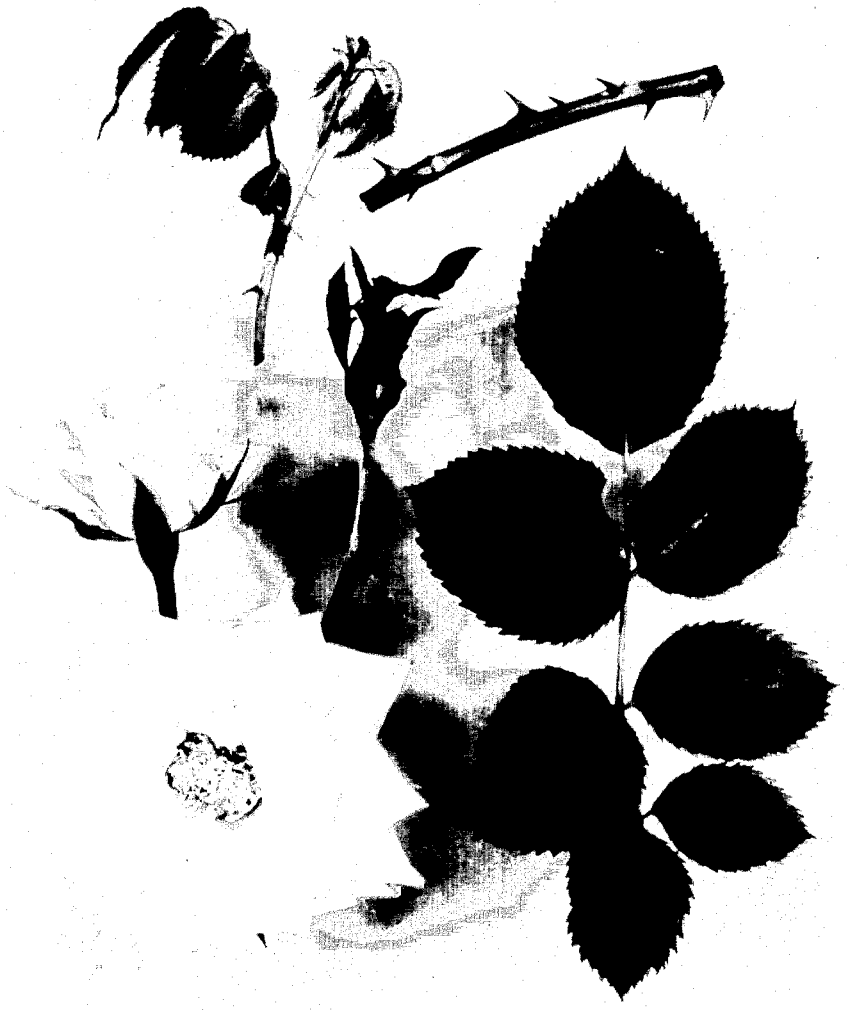
Inventor.
E. S. Boerner
By: Robb & Robb
Attorneys.

United States Patent Office

Plant Pat. 2,634
Patented May 24, 1966

2,634
ROSE PLANT

Eugene S. Boerner, Newark, N.Y., assignor to Jackson & Perkins Company, Newark, N.Y., a corporation of New York Filed Apr. 23, 1965, Ser. No. 450,565
1 Claim. (Cl. Plt.—26)

The present invention relates to a new and distinct variety of rose plant of the floribunda class, which was originated by me by crossing an unnamed and unpatented seedling of "Pinocchio" (Plant Patent No. 484) with another unnamed and unpatented seedling derived from a cross of "Red Pinocchio" (Plant Patent No. 812) × "Garnette" (unpatented).

The primary objective of the breeding was to produce a new and improved rose variety suitable for greenhouse use for cut flower production and which corresponds to the "Garnette" type of rose variety. This objective was fully achieved, along with other desirable improvements, as evidenced by the following unique combination of characteristics which are outstanding in the new variety and which distinguish it from its parents, as well as from all other varieties of which I am aware:

(1) A very free blooming habit;

(2) An unusual flower stem length for flowers of this type;

(3) Stiff flower petals;

(4) An unusual pink color for a floribunda rose, said color corresponding to Rose Pink overcast with Rosolane Pink; and (5) Very long lasting flower qualities.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
- *Seed parent.*—An unnamed seedling of "Pinocchio."
- *Pollen parent.*—An unnamed seedling of "Red Pinocchio" × "Garnette."

Classification:
- *Botanic.*—Floribunda.
- *Commercial.*—Floribunda.

*Flower*

(Observations made from specimens grown in greenhouse at Newark, New York, in the early morning during the first part of November.)

Blooming habit:
- *Recurrent.*—Continuous and profusely.
- *Other habit.*—Long lasting flowers bloom very freely.

Bud:
- *Size.*—Medium.
- *Form.*—Ovoid; not affected by wet or hot weather.
- *Color.*—When sepals first divide—Spinel Red, Plate 26. When petals begin to unfurl—Spinel Pink, Plate 26, lightly overcast with Spinel Red, Plate 26. When half-blown; Inside of petals—Rose Color, Plate 12, very lightly overcast with Deep Rose Pink, Plate 12; reverse of petals—Deep Rose Pink, Plate 12, lightly overcast with Rose Color, Plate 12.

- *Sepals.*—Branched; curl back when petals begin to unfurl. Color: Inside—Malachite Green, Plate 32; outside—Light Hellebore Green, Plate 17.
- *Calyx.*—Color—Biscay Green, Plate 31. Shape—pear. Size—small. Aspect—smooth. Odor when rubbed—none.
- *Peduncle.*—Length—medium. Aspect—smooth. Strength—erect; slender. Color—Biscay Green, Plate 31.
- *Opening.*—Opens up well; is not affected by adverse weather conditions.

Bloom:
- *Size.*—Medium. Average size when fully expanded—3½ inches to 4 inches.
- *Borne.*—Both singly and several together.
- *Stems.*—Long; strong.
- *Form (when first open).*—Cupped. Permanence—retains its form to the end, but opens.
- *Petalage.*—Double (full but open center). Number of petals under normal conditions—from 25 to 30.
- *Color.*—Center of flower—Deep Rose Pink, Plate 12. Outer petals—Rose Pink, Plate 12, very lightly overcast with Rosolane Pink, Plate 26. Base of petals (aiglet)—Citron Yellow, Plate 16. Inside of petals—Rose Pink, Plate 12, overcast with Rosolane Pink, Plate 26. Reverse of petals—Deep Rose Pink, Plate 12, overcast with Rose Pink, Plate 12. General tonality from a distance—Rose Pink, Plate 12, overcast with Rosolane Pink, Plate 26.
- *Discoloration.*—General tonality at end of first day—Rose Pink, Plate 12, overcast with Rosolane Pink, Plate 26. Second day—Rose Pink, Plate 12, overcast with Rosolane Pink, Plate 26. Third day—Rose Pink, Plate 12.

Petals:
- *Texture.*—Leathery and stiff.
- *Appearance.*—Inside—satiny. Outside—shiny.
- *Form.*—Oval.
- *Arrangement.*—Imbricated (regularly arranged shingle-like).
- *Petaloids in center.*—Few; small.
- *Persistance.*—Drop off cleanly.
- *Fragrance.*—Moderate. Nature—fruity (russet apple).
- *Lasting quality.*—On the plant—very long. As cut flower—very long.

*Genital organs*

Stamens, anthers: Medium size; many; arranged regularly around styles. Color—Capucine Buff, Plate 3.

Stamens, filaments (threads): Medium length. Color—Thulite Pink, Plate 26.

Pollen: Color—Pale Yellow-Orange, Plate 3.

Styles: Loosely separated; uneven length; medium length; thin.

Stigmas: Color—cream color.

Ovaries: All enclosed in calyx.

Hips: None.

Seeds: None.

*Plant*

Form: Bush.

Growth: Vigorous; upright and branching.

Foliage: Compound of 5 to 7 leaflets.
- *Size.*—Medium.
- *Quantity.*—Normal.
- *Color.*—New foliage: Upper side—Hessian Brown, Plate 13, with center rib Yellowish-Oil Green, Plate 5; under side—Van Dyke Red, Plate 13. Old foliage: Upper side—Dark Cress Green, Plate 31; under side—Light Elm Green, Plate 17.

*Shape.*—Oval pointed.
*Texture.*—Upper side—leathery. Under side—smooth.
*Ribs and veins.*—Ordinary.
*Edge.*—Serrated (saw toothed).
*Serration.*—Both double and single; sharp.
*Leaf stem.*—Color—Light Elm Green, Plate 17. Under side—prickly.
*Stipules.*—Medium length; smooth.

Wood:
*New wood.*—Color—Lettuce Green, Plate 5. Bark—smooth.
*Old wood.*—Color—Cress Green, Plate 31. Bark—smooth.

Thorns:
*Thorns.*—Quantity: On main stalks from base—ordinary; on laterals from stalk—ordinary. Form—narrow base; short; hooked downward.

Color (when young)—Old Rose, Plate 13.
*Prickles.*—Quantity: On main stalks—none; on laterals—none.
*Short needles.*—Quantity: On main stalks—none; on laterals—none.

I claim:

A new and distinct variety of rose plant of the floribunda class, substantially as herein shown and described, characterized particularly as to novelty by the unique combination of a very free blooming habit, an unusual flower stem length for flowers of this type, stiff flower petals, an unusual pink color for a floribunda rose, said color corresponding to Rose Pink overcast with Rosolane Pink, and very long lasting flower qualities.

No references cited.

ABRAHAM G. STONE, *Primary Examiner.*